US006824977B2

(12) United States Patent
Zucker-Franklin et al.

(10) Patent No.: US 6,824,977 B2
(45) Date of Patent: Nov. 30, 2004

(54) ASSAYS FOR HUMAN T CELL LYMPHOTROPHIC VIRUS TYPES I AND II

(75) Inventors: Dorothea Zucker-Franklin, New York, NY (US); Bette A. Pancake, Somerset, NJ (US)

(73) Assignee: New York University, New York, NY (US)

( * ) Notice: Subject to any disclaimer, the term of this patent is extended or adjusted under 35 U.S.C. 154(b) by 0 days.

(21) Appl. No.: 09/543,782

(22) Filed: Apr. 6, 2000

(65) Prior Publication Data

US 2002/0042053 A1 Apr. 11, 2002

Related U.S. Application Data

(60) Provisional application No. 60/127,956, filed on Apr. 6, 1999.

(51) Int. Cl.[7] ........................ C12Q 1/68; G01N 33/537; G01N 33/543; C12P 19/34; C07K 1/00

(52) U.S. Cl. ........................... 435/6; 435/7.1; 435/7.92; 435/91.1; 435/91.2; 530/350

(58) Field of Search ............................ 435/6, 7.1, 7.92, 435/91.1, 91.2, 2; 530/350; 935/77, 78; 436/501, 504

(56) References Cited

U.S. PATENT DOCUMENTS 4,588,681 A 5/1986 Sawada et al.

OTHER PUBLICATIONS

Zucker–Franklin et al. Reexamination of human t cell lymphotropic virus (HTLV–I/II) prevalence. Proc. Natl. Acad. Sci. USA. vol. 94, No. 12, pp. 6403–6407, Jun. 1997.*

Abstract of Amichai, et al., "Hypopigmented Mycosis Fungoides in a White Female," *J. Dermatol* 23(6):425–426 (1996).

Abstract of Arnett, et al., "The American Rheumatism Association 1987 Revised Criteria for the Classification of Rheumatoid Arthritis," *Arthritis Rheum.* 31(3):315–324 (1988).

Abstract of Benvenisty, et al., "Brain Tumors and Lymphomas in Transgenic Mice that Carry HTLV–I LTR/c–myc and lg/tax Genes," *Oncogene* 7(12):2399–2405 (1992).

Blattner, "Human T–Lymphotrophic Viruses and Diseases of Long Latency," *Annals of Internal Medicine* 111(1):4–6 (1989).

Abstract of Breathnach, et al., "Hypopigmented Mycosis Fungiodes: Report of Five Cases with Ultrastructural Observations," *Br. J. Dermatol* . 106(6):643–649 (1982).

Abstract of Buckle, et al., "HTLV–I–induced T–cell Activation," *J. Acquir. Immune Defic. Syndr. Hum. Retroviral* 13 Suppl 1:S107–113 (1996).

Center for Disease Control and Prevention (CDCP), "Licensure of Screening Tests for Antibody to Human T–Lymphotrophic Virus Type" *Morbid, and Mortal. Weekly Report* 37:736–747 (1988).

Abstract of Chen, et al., "Sexual Transmission of Human T–Cell Leukemia virus Type I Associated with the Presence of Anti–Tax Antibody," *Proc. Natl. Acad. Sci. USA* 88(4):1182–1186 (1991).

Abstract of Copeland, et al., "Envelope Proteins of Human T cell Leukemia Virus Type I: Characterization by Antisera to Synthetic Peptides and Identification of a Natural Epitope," *J. Immunol.* 137(9):2945–2951 (1986).

Abstract of Eguchi, et al., "High Seroprevalence of Anti–HTLV–I Antibody in Rheumatoid Arthritis," *Arthritis Rheum.* 39(3):463–466 (1996).

Abstract of Ehrlich, et al., "Detection of Anti–HTLV–I Tax Antibodies in HTLV–I Enzyme–linked Immunosorbent Assay–negative Individuals," *Blood* 74(3):1066–1072 (1989).

Abstract of Eiraku, et al., "Identification and Characterization of a New and Distinct Molecular Subtype of Human T–cell Lymphotropic Virus Type," *J. Virol.* 70(3):1481–1492 (1996).

Abstract of El–Hoshy, et al., "Adolescence Mycosis Fungoides: An Annual Presentation with Hypopigmentation," *J. Dermatol.* 22(6):424–427 (1995).

Franchini, "Molecular Mechanisms of Human T–Cell Leukemia/Lymphotropic Virus Type I Infection," *Blood* 86(10):3619–3639 (1995).

Abstract of Gessain, et al., "Antibodies to Human T–lymphotropic Virus Type–I in Patients with Tropical Spatsic Paraparesis," *Lancet* 2(8452):407–410 (1985).

Abstract of Ghosh, et al., "Human T–cell Leukemia Virus Type I Tax/Rex DNA and RNA in Cutaneous T–cell Lymphoma," *Blood* 84(8):2663–2671 (1994).

Gitlin, et al., "The Molecular Biology of Human T–cell Leukemia Viruses," *Human Retroviruses* Cullen (ed), IRL Press/Oxford Univ. Press New York, 1993) pp. 159–192.

Abstract of Goldberg, et al., "Hypopigmented Mycosis Fungoides. Speculations About the Mechanism of Hypopigmentation," *Am. J. Dermatopathol.* 8(4):326–330 (1986).

(List continued on next page.)

*Primary Examiner*—Jeffrey Fredman
*Assistant Examiner*—Teresa Strzelecka
(74) *Attorney, Agent, or Firm*—Browdy and Neimark, P.L.L.C.

(57) ABSTRACT

Blood or other body fluid is screened for infection of an individual with HTLV-I and/or HTLV-II by subjecting each sample from the individual to a test for the presence of the Tax protein, DNA which encodes the Tax protein, or antibodies specific to the Tax protein, and correlating the presence of HTLV-I and/or HTLV-II infection with the result of the test. This test can also be used to screen pregnant women and nursing mothers for HTLV-I/II infection, or to screen seronegative patients who otherwise present symptoms of HTLV-I/II infection for HTLV-I/II infection. Because this test, which relies on testing for the presence of the tax protein is so specific for HTLV-I and/or HTLV-II infection, there is no requirement for input from any other test result to test positively for HTLV-I and/or HTLV-II.

1 Claim, 10 Drawing Sheets

OTHER PUBLICATIONS

Abstract of Hall, et al., "Deletec HTLV–I Provirus in Blood and Cutaneous Lesions of Patients with Mycosis Fungoides," *Science* 253(5017):317–320 (1991).
Abstract of Hall, et al., "Multiple Isolates and Characteristics of Human T–cell Leukemia Virus Type II," *J. Virol.* 66(4):2456–2463 (1992).
Abstract of Hall, et al., "Human T Lymphotropic Virus Type II (HTLV–II): Epidemiology, Molecular Properties, and Clinical Features of Infection," *J. Acquir. Immune Defic. Syndr. Hum. Retrovirol.* 13 Suppl 1:S204–214 (1996).
Abstract of Hanfield–Jones, et al., "Hypopigmented Mycosis Fungoides," *Clin. Exp. Dermatol.* 17(5):374–375 (1992).
Abstract of Hinuma, et al., "Adult T–cell Leukemia: Antigen in an ATL Cell Line and Detection of Antibodies to the Antigen in Human Sera," *Proc. Natl. Acad. Sci. USA* 78(10):6476–6480 (1981).
Abstract of Hirose, et al., "Milk–borne Transmission of Human T–cell Leukemia Virus Type I in Rabbits," *Virology* 162(2):487–489 (1988).
Iwahara, et al., "Transmission of HTLV–I to Rabbits via Semen and Breast Milk from Seropositive Healthy Persons," *Int. J. Cancer* 45:980–983 (1990).
Abstract of Iwakura, et al., "Induction of Inflammatory Arthropathy Resembling Rheumatoid Arthritis in Mice Transgenic for HTLV–I," *Science* 253(5023):1026–1028 (1991).
Abstract of Iwakura, et al., "Autoimmunity Induction by Human T–cell Leukemia Virus Type I in Transgenic Mice that Develop Chronic Inflammatory Arthropathy Resembling Rheumatoid Arthritis in Humans," *J. Immunol.* 155(3):1588–1598 (1995).
Abstract of Jeang, et al., "Abundant Synthesis of Functional Human T–cell Leukemia Virus Type I p40x Protein in Eucaryotic Cells by Using a Baculovirus Expression Vector," *J. Virol.* 61(3):708–713 (1987).
Abstract of Kamihira, et al., "Antibodies Against p40tax Gene Product of Human T–lymphotropic Virus Type–I (HTLV–I) Under Various Conditions of HTLV–I Infection," *Jpn. J. Cancer Res.* 80(11):1066–1071 (1989).
Abstract of Kanner, et al., "Human Retroviral env and gag Polypeptides: Serologic Assays to Measure Infection," *J. Immunol.* 137(2):674–678 (1986).
Abstract of Kashiwagi, et al., "Antibody to p40tax Protein of Human T cell Leukemia Virus 1 and Infectivity," *J. Infect. Dis.* 161(3):426–429 (1990).
Khan, et al,. "Localization of Human T–Cell Lymphotropic Virus–1 tax Proviral Sequences in Skin Biopsies of Patients with Mycosis Fungoides by in situ Polymerase Chain Reaction," *The Journal of Investigative Dermatology* 106:667–672 (1996).
Abstract of Kinoshita, et al., "Demonstration of Adult T–cell Leukemia Virus Antigen in Milk from Three Sero–Positive Mothers," *Gann.* 75(2):103–105 (1984).
Abstract of Kitajima, et al., "Synthesis of Proteins in *Eschericia coli* Immunoreactive with Sera from Individuals Infected with Human t–cell Leukemia Virus Type I," *Mol Cell. Probes* 2(1):39–46 (1988).
Abstract of Kitajima, et al., "Detection of Human T cell Lymphotropic Virus type I Proviral DNA and its Gene Expression in Synovial Cells in Chronic Inflammatory Arthropathy," *J. Clin. Invest.* 88(4):1315–1322 (1991).
Abstract of Kerber, et al., "Polymerase Chain Reaction Analysis of Defective Human T–cell Leukemia Virus Type I Proviral Genomes in Leukemic cells of Patients with Adult T–cell Leukemia," *J. Virol.* 65(10):5471–5476 (1991).
Abstract of Kwok, et al., "Characterization of a Sequence of Human T cell Leukemia Virus Type I from a Patient with Chronic Progressive Myelopathy," *J. Infect. Dis.* 158(6):1193–1197 (1988).
Abstract of Lal, "Delineation of Immunodominant Epitopes of Human T–lymphotropic Virus Types I and II and Their Usefulness in Developing Serologic Assays for Detection of Antibodies to HTLV–I and HTLV–II," *J. Acquir Immune Defic. Syndr. Hum. Retrovirol* 13 Suppl 1:S170–178 (1996).
Abstract of Lambroza, et al. "Hypopigmented Variant of Mycosis Fungoides: Demography, Histopathology, and Treatment of Seven Cases," *J. Am. Acad. Dermatol.* 32(6):987–993 (1995).
Abstract of Lee, et al,. "Relative Prevalence and Risk Factors of HTLV–I and HTLV–II Infection in US Blood Donors," *Lancet* 337(8755):1435–1439 (1991).
Abstract of Lee, et al,. "Complete Nucleotide Sequence of HTLV–II Isolate NRA: Comparison of Envelope Sequence Variation of HTLV–II Isolates from U.S. Blood Donors and U.S. and Italian i.v. Drug Users," *Virology* 196(1):57–69 (1993).
Abstract of Manca, et al., "Persistence of Human T cell Lymphotropic Virus Type I (HTLV–1) Sequences in Peripheral Blood Mononuclear Cells from Patients with Mycosis Fungoides," *J. Exp. Med.* 180(5):1973–1978 (1994).
Abstract of Mariette, et al,. "Detection of Human T lymphotropic Virus Type I Tax Gene in Salivary Gland Epithelium from Two Patients with Sjogren's Syndrome," *Arthritis Rheum.* 36(10):1423–1428 (1993).
Abstract of McCallum, et al., "Arthritis Syndromes Associated with Human T–cell Lymphotropic Virus Type I Infection," *Med. Clin. North Am.* 81(1):261–276 (1997).
Misch, et al., "Hypopigmented Mycosis Fungiodes," *Clinical and Experimental Dermatology* 12:53–55 (1987).
Miyoshi, et al., "Type C Virus Particles in a Cord T–cell Line Derived by Co–cultivating Normal Human Cord Leukocytes and Human Leukaemic T cells," *Nature* 294:770–771 (1981).
Abstract of Mochizuki, et al., "Uveitis Associated with Human T–cell Lymphotropic Virus Type," *Am. J. Ophthalmol.* 114(2):123–129 (1992).
Mowat, "The Regulation of Immune Responses to Dietary Protein Antigens," *Immunology Today* 8(3):93–98 (1987).
Abstract of Myrie, et al., "Light–microscopic Analysis of Sectioned Sezary Cells: An Accurate Alternative to Electron Microscopy," *Am. J. Pathol.* 99(1):243–252 (1980).
Abstract of Nerenberg, et al., "The tat Gene of Human T–lymphotropic Virus Type 1 Induces Mesenchymal Tumors in Transgenic Mice," *Science* 237(4820):1324–1329 (1987).
Abstract of Nishioka, "HTLV–I Arthropathy and Sjorgen Syndrome," *J. Acquir. Immune Defic. Syndr. Hum. Retrovirol* 13 Suppl 1:S57–62 (1996).
Abstract of Ohshima, et al., "Defective Provirus form of Human T–cell Leukemia Virus Type I in Adult T–cell Leukemia/Lymphoma: Clinicopathological Features," *Cancer Res.* 51(17):4639–4642 (1991).
Abstract of Okayama, et al., "Unusual Pattern of Antibodies to Human T–cell Leukemia Virus Type–I in Family Members of Adult T–cell Leukemia Patients," *Blood* 78(12):3323–3329 (1991).
Osame, et al., "HTLV–I Associated Myelopathy, A New Clinical Entity," *Lancet* I:1031–1032 (1986).
Abstract of Osame, et al., "Chronic Progressive Myelopathy Associated with Elevated Antibodies to Human T–lymphotropic Virus Type I and Adult T–cell Leukemialike Cells," *Ann. Neurol.* 21(2):117–122 (1987).

Pancake, et al., "The Cutaneous T Cell Lymphoma, Mycosis Fungoides, is a Human T Cell Lymphotropic Virus–associated Disease," *J. Clin. Invest*. 95:547–554 (1995).
Abstracts of Pancake, et al., "The Difficulty of Detecting HTLV–1 Proviral Sequences in Patients with Mycosis Fungoides," *J. Acquir. Immune Defic. Syndr. Hum. Retrovirol*. 13(4):314–319 (1996).
Pancake, et al., "Demonstration of Antibodies to Human T–cell Lymphotropic Virus–I tax in Patients with the Cutaneous T–Cell Lymphoma, Mycosis Fungoides, Who are Seronegative for Antibodies to the Structural Proteins of the Virus," *Blood* 88(8):3004–3009 (1996).
Poiesz, et al., "Detection and Isolation of Type C Retrovirus Particles from Fresh and Cultured Lymphocytes of a patient with Cutaneous T–cell Lymphoma," *Proc. Natl. Acad. Sci. USA* 77(12):7415–7419 (1980).
Abstract of Popovic, et al., "Isolation and Transmission of Human Retrovirus (Human T–cell Leukemia Virus)," *Science* 219(4586):856–859 (1983).
Abstract of Ramirez, et al., "Defective Human T–cell Lymphotropic Virus Type I (HTLV–I) Provirus in 10 Chilean Seronegative Patients with Tropical Spastic Paraparesis or HTLV–I–associated Myelopathy," *J. Clin. Microbiol*. 36(6):1811–1813 (1998).
Ratnam, et al., "Clinico–pathological Study and Five–year Follow–up of 10 Cases of Hypopigmented Mycosis Fungoides," *Journal of the European Academy of Dermatology and Venereology* 3:505–510 (1994).
Abstract of Sawada, et al., "High Risk of Mother–to–Child Transmission of HTLV–I in p40tax Antibody–Positive Mothers," *Jpn. J. Cancer Res*. 80(6):506–508 (1989).
Abstract of Saxinger, et al., "Methods in Laboratory Investigation. Application of the Indirect Enxyme–linked Immunosorbent Assay Microtest to the Detection and Surveillance of Human T cell Leukemia–Lymphoma Virus," *Lab Invest* 49(3):371–377 (1983).
Abstract of Saxon, et al., "T–lymphocyte Variant of Hairy–cell Leukemia," *Ann. Intern. Med*. 88(3):323–326 (1978).
Abstract of Seike, et al., "Human Adult T–cell Leukemia Virus: Complete Nucleotide Sequence of the Provirus Genome Integrated in Leukemia cell DNA," *Proc. Natl. Acad. Sci. USA* 80(12):3618–3622 (1983).
Abstract of Shimotohno, et al., "Complete Nucleotide Sequence of an Infectious Clone of Human T–cell Leukemia Virus Type II: An open Reading Frame for the Protease Gene," *Proc. Natl. Acad. Sci. USA* 82(10):3101–3105 (1985).
Abstract of Shioiri, et al., "Analysis of Anti–Tax Antibody of HTLV–I Carriers in an Endemic Area in Japan," *Int. J. Cancer* 53(1):1–4 (1993).
Sigal, et al., "Hypopigmented Mycosis Fungoides," *Clinical and Experimental Dermatology* 12:453–454 (1987).
Abstract of Smith, et al., "Single–step Purification of Polypeptides Expressed in *Escherichia coli* as Fusions with Glutathione S–transferase," *Gene* 67(1):31–40 (1988).
Abstract of Sodroski, et al., "Trans–acting Transcriptional Activation of the Long Terminal Repeat of Human T Lymphotropic Viruses Infected Cells," *Science* 225(4660):381–385 (1984).
Abstract of Sumida, et al., "Expression of Sequences Homologous to HTLV–I tax Gene in the Labial Salivary Glands of Japanese Patients with Sjogren's Syndrome," *Arthritis Rheum*. 37(4):545–550 (1994).
Abstract of Terada, et al., "Prevalence of Serum and Salivary Antibodies to HTLV–1 in Sjogren's Syndrome," *Lancet* 344(8930):1116–1119 (1994).
Abstract of Vanderlugt, et al., "Epitope Spreading," *Curr. Opin. Immunol*. 8(6):831–836 (1996).
Abstract of von Herrath, et al., "Virus–induced Autoimmune Disease," *Curr. Opin. Immunol*. 8(6):878–885 (1996).
Abstract of Wattel, et al., "Clonal Expansion of Infected Cells: A Way of Life for HTLV–I," *J. Acquir. Immune. Defic. Syndr. Hum. Retrovirol*. 13 Suppl 1:S92–99 (1996).
Abstract of Weiner, et al., "Oral Tolerance: Immunologic Mechanisms and Treatment of Animal and Human Organ–specific Autoimmune Diseases by Oral Administration of Autoantigens," *Annu. Rev. Immunol*. 12:809–837 (1994).
Abstract of Williams, et al., "Seroprevalence and Epidemiological Correlates of HTLV–I Infection in U.S. Blood Donors," *Science* 240(4852):643–646 (1988).
Abstract of Wong–Staal, et al.,"A Survey of Human Leukaemias for Sequence of a Human Retrovirus," *Nature* 302(5909):626–628 (1983).
Yoshida, "B. Retroviruses (HTLVs)," *The Molecular Basis of Blood Diseases* Stamatoyannopoulos et al. (eds), W.B. Saunders (Philadelphia) pp. 929–941, (1987).
Yoshida, et al., "Molecular Biology of Human T–Cell Leukemia Virus Associated with Adult T–Cell Leukemia," *Current Topics in Microbiology and Immunology* 115:157–175 (1985).
Abstract of Zackheim, et al., "Mycosis Fungoides Presenting as Areas of Hypopigmentation: A report of three cases," *J. Am Acad. Dermatol*. 6(3):340–345 (1982).
Abstract of Zackheim, et al., Mycosis Fungoides with Onset Before 20 years of Age,: *J. Am. Acad. Dermatol*. 36(4):557–562 (1997).
Zucker–Franklin, et al., "Ultrastructural, Immunologic, and Functional Studies on Sézary Cells: A Neoplastic Variant of Thymus–Derived (T) Lymphocytes," *Proc. Nat. Acad. Sci. USA* 71(5):1877–1881 (1974).
Abstract of Zucker–Franklin, et al., "Detection of Human T–lymphotropic Virus–like Particles in Cultures of Peripheral Blood Lymphocytes from Patients with Mycosis Fungoides," *Proc. Natl. Acad. Sci. USA* 88(17):7630–7634 (1991).
Abstract of Zucker–Franklin, et al., "Human Lymphotropic Retroviruses Associated with Mycosis Fungoides: Evidence that Human T–cell Lymphotropic Virus Type II (HTLV–II) as well as HTLV–I May Play a Role in the Disease," *Blood* 80(6):1537–1545 (1992).
Zucker–Franklin, et al., "Cutaneous Disease Resembling Mycosis Fungoides in HIV–Infected Patients Whose Skin and Blood Cells also Harbor Proviral HTLV Type I," *AIDS Research and Human Retroviruses* 10(9):1173–1177 (1994).
Zuxker–Franklin, et al., "Reexamination of Human T cell Lymphotropic Virus (HTLV–I/II) Prevalence," *Proc. Natl. Acad. Sci. USA* 94:6403–6407 (1997).
Zucker–Franklin, et al., "HTLV–I Provirus in Seronegative Healthy Blood Donors," *The Lancet* 349:999 (1997).
Abstract of Zucker–Franklin, et al., "Human T–cell Lymphotropic Virus Type 1 tax Among American blood Donors," *Clin. Diagn. La. Immunol*. 5(6):831–835 (1998).

* cited by examiner

```
SEQ ID NO:1  HTLV-I   5'-AAGGCGACTGGTGCCCCATCTCTGGGGGACTATGTTCGGCCCGC
             Donors      ---------------------------------------------
             HTLV-II     -G-C---T-----T--G----A--T--T-------CA-----

             HTLV-I   CTACATCGTCACGCCCTACTGGCCACCTGTCCAGAGCATCAGAT-3'
SEQ ID NO:2  Donors   ---------------------------------------------
             HTLV-II  -------A--T----C------------------------C--AC-
```

FIGURE 3A

```
             HTLV-I   5'-AAGGCGACTGGTGCCCCATCTCTGGGGGACTATGTTCGGCCCGC
SEQ ID NO:3  1           -G-C---T-----T-------A---T--T---------CA-----
             2           ---------T-----T-----------T----------------
             HTLV-II     -G-C---T-----T---G---A---T--T---------CA-----

             HTLV-I   CTACATCGTCACGCCCTACTGGCCACCTGTCCAGAGCATCAGAT-3'
SEQ ID NO:4  1        ---------A--T-----C--------------------C--A C-
             2        ---------A--T-----C-----------------------A --
             HTLV-II  ---------A--T----C----------------------C- A C-
```

```
                HTLV-I   5'-AAGGCGACTGGTGCCCCATCTCTGGGGGACTATGTTCGGCCCGC
SEQ ID NO: 1    patient     ------------------------------------------  -
                mother      ------------------------------------------  -
                HTLV-II     -G-C---T-----T---G----A--T--T--------CA--- -

                HTLV-I      CTACATCGTCACGCCCTACTGGCCACCTGTCCAGAGCATCAGAT-3'
SEQ ID NO: 2    patient     ---------------------------------------------
                mother      ---------------------------------------------
                HTLV-II     ---------A--T----C--------------------C--AC-
```

FIGURE 8

ASSAYS FOR HUMAN T CELL LYMPHOTROPIC VIRUS TYPES I AND II

This application claims the benefit of a Provisional Patent Application No. 60/127,956, filed on Apr. 6, 1999.

FIELD OF THE INVENTION

The present invention is directed to methods for screening for HTLV-I and HTLV-II.

BACKGROUND OF THE INVENTION

Human T cell lymphotropic virus type I (HTLV-I) is known to be the cause of neoplastic diseases, such as adult T cell leukemia/lymphoma (ATLL), as well as of fatal demyelinating disorders, such as tropical spastic paraparesis and HTLV-I-associated myelopathy (TSP/HAM) (Gessain et al, 1985; Osame et al, 1987), which are non-neoplastic inflammatory/autoimmune conditions. While the majority of affected patients have antibodies, more recent studies have identified HTLV-I antibody negative cases of ATLL (Poiesz et al, 1980; Hinuma et al, 1981; Miyoshi et al, 1981) and TSP/HAM cases occur (Korber et al, 1991; Ohshima et al, 1991; Ramirez et al, 1998). Transmission of the virus is mediated by transfusion of virus-harboring leukocytes in blood and breast milk, as well as sexually, from male to female. Perinatal transmission occurs also in 5% of non-breast-fed children of healthy virus-carrying mothers (Gessain et al, 1985). In contrast to HIV, free virus particles do not seem to be infectious. However, following transfusion of cellular blood components harboring HTLV-I, 44 to 64% of recipients seroconvert (Osame et al, 1986; Blattner, 1989; Yoshida, 1994. For this reason, all blood used for transfusion in the USA has been screened for antibodies to the structural proteins of HTLV since 1988. This is done using ELISA or Western blot techniques using viral lysates which identify antibodies to the structural proteins of the virus, such as HTLV-I/II core (gag) protein p24 and envelope (Env) proteins gp46, gp64/68.

On the basis of the above testing, the prevalence of HTLV-I infection among Americans without obvious risk factors, such as being from an endemic region or intravenous drug abuse, has been estimated to be about 0.016% (Lee et al, 1991). It may be as high as 0.1% in some locations (Williams et al, 1988). One suspects that infection with HTLV-I infection among Caucasian Americans may be higher than determined by routinely used methods in light of studies on cutaneous T cell lymphoma mycosis fungoides (MF) (Zucker-Franklin et al, 1991; Pancake et al, 1995). MF patients usually do not have antibodies to the structural proteins of the virus, but harbor proviral sequences of HTLV-I in their peripheral blood mononuclear cells and skin (Zucker-Franklin, 1991; Pancake et al, 1995; Zucker-Franklin, 1994; Khan et al, 1996). A high percentage of these patients were also shown to have antibodies to HTLV-I Tax (Pancake et al, 1996b), an antigen not included in commercially available HTLV serologic tests.

A study was conducted of healthy relatives of MF patients who were serologically negative for antibodies to HTLV-I when their specimens were tested at a major blood transfusion center (Zucker-Franklin et al, 1997a). Of the first eight individuals tested, six proved to have tax sequences in the PBMCs and antibodies to the Tax antigen by Western blot analysis. Since family studies of a relatively rare disease manifested mostly in middle-aged and elderly individuals are time-consuming, a more expeditious approach was chosen to determine whether currently used serologic methods are adequate to establish the true prevalence of HTLV infection among blood donors.

Accordingly, a cohort of individuals among whom the prevalence of HTLV infection was known to be high, i.e., known injection drug users (IDUs) was selected for study (Zucker-Franklin et al, 1997b). Matched sera and PBMCs obtained from 81 HIV-negative methadone clinic attendees were tested by routine serologic methods, as well as for tax, pol, and gag proviral sequences by PCR/Southern blot analysis and antibodies to viral structural proteins, as well as to the Tax gene product. Routine serology proved 18/81 (22%) of these specimens to be positive for antibodies to HTLV, which concurred with results obtained by other investigators. On the other hand, 39/81 (48.1%) were found positive for HTLV proviral sequences by biomolecular means, and 42 (51.8%) were positive when both serologic tests and PCR/Southern blot analyses were used. Together, the results of these studies suggested that the prevalence of infection with HTLV, particularly when efforts are made to detect Tax sequences, may be considerably higher than is currently believed.

Food and Drug Administration-approved blood screening assays are available which may be used to detect the presence of HTLV-I antibodies in blood samples. Available screening assays are discussed in CDCP (1988). These assays typically use viral antigenic proteins isolated from mammalian cell cultures which are infected with HTLV-I. Other assays are reported in Sawada et al, U.S. Pat. No. 4,588,681; Essex et al, PCT Publication WO 84/04327; Copeland et al (1986); Saxinger et al (1983); Bodner et al, EPA 1035352; and Hare et al, PCT Publication WO 91/07510, the entire contents of all of which are hereby incorporated by reference.

However, many people infected with HTLV-I or -II have lost the sequences which encode the structural components of the virus. While these individuals have antibodies to Tax, they test negative for antibodies to HTLV by tests which are currently used in blood banks (Zucker-Franklin et al, 1997a; Zucker-Franklin et al, 1997b; Ehrlich, 1989; Shiori, 1993; Pancake, 1996b). Thus, their blood is considered safe for transfusion.

Some of the problems associated with use of HTLV-I proteins derived from infected mammalian cells may be overcome by applying recombinant DNA methods and techniques to develop antigenic polypeptides in non-mammalian host cells.

HTLV-I assays using recombinant antigenic polypeptides have been described. Lal et al (1996) have made antigenic polypeptides. Antigenic polypeptides expressed in *E. coli* transformed with portions of the gag gene may be used in an immunodot assay. The sensitivity of this immunodot assay was described as being comparable to Western blots, and the results were described as being as reliable as radioimmunoassays (Kanner et al, 1986). Itoh et al, in U.S. Pat. No. 4,795,805, disclose another assay using antigenic polypeptides encoded by the gag gene.

WO 91/07510 of Amgen Inc. discloses the use of one or more recombinant polypeptide antigens which are polypeptides encoded by all or part of the env, tax or gag genes of HTLV-I. There is no suggestion therein that the use of any one of these antigens is better than either of the others.

Other HTLV-I derived recombinant antigenic polypeptides have also been used in immunoassays. Cell lysates containing either a 59 kD fusion polypeptide encoded by about half of the env gene and about three-quarters of the tax gene or a single 100 kD fusion polypeptide encoded by gag, env, and tax gene fragments reacted with sera from an HTLV-I infected patient using a Western blot analysis (Kitajima et al, 1988).

A sensitive HTLV-I assay which uses recombinant antigenic polypeptides requires antigens which are readily available and which are immunologically reactive with antibodies found in all or nearly all seropositive individuals. These antigenic polypeptides must be readily purified in order to avoid or eliminate non-specific binding to contaminating host cell proteins by cross-reactive antibodies which may be present in body fluid samples. These antigenic polypeptides must also retain their immunological activity when they are used to prepare immunoassay apparatus which typically involve adsorption of the antigenic polypeptides onto a solid support and contacting the adsorbed polypeptides which various blocking and washing reagents.

It has previously been believed that a sensitive HTLV-I assay requires more than one antigen in a single assay in order to detect individuals exposed to HTLV-I that have different antibody profiles. Hare et al, PCT WO 91/07510, note that for any given seropositive population, individuals exhibit different immunogenic responses to viral antigens, and an assay using only one antigen may not detect all of the exposed individuals. Thus, Hare et al use a single screening assay using more than one antigen in order to ensure all exposed individuals are detected, having found that an immunoassay employing only a single antigen would not be able to accurately identify all infected serum samples (page 9, lines 5–7). This assay is limited to assaying for HTLV-I and requires a separate assay to test for HTLV-II.

Therefore, there is a need for a simple assay which would accurately identify all infected serum samples for HTLV-I and/or HTLV-II infection.

SUMMARY OF THE INVENTION

It is an object of the present invention to overcome the aforesaid deficiencies in the prior art.

It is another object of the present invention to provide a single assay for HTLV-I and/or HTLV-II in serum samples.

It is another object of the present invention to provide a method for screening blood donors or potential blood donors for carriers of disease or conditions related to HTLV-I and/or HTLV-II infection.

It is a further object of the present invention to provide a method for screening pregnant women and nursing mothers for infections related to HTLV-I and/or HTLV-II infection.

It is another object of the present invention to provide a method for screening patients for HTLV infection when the patients do not test positive for antibodies to HTLV.

According to the present invention, blood or other body fluid of a given population is screened for infection or past infection with HTLV-I and/or HTLV-II by subjecting each sample to a test for the presence of the HTLV-I or HTLV-II Tax protein, DNA which encodes the Tax protein, or antibodies specific to the subject Tax protein; and correlating the presence of HTLV-I and/or HTLV-II infection with the result of the test. Because this test, which relies on testing for the presence of the HTLV-I or HTLV-II Tax protein, is so specific for HTLV-I and/or HTLV-II infection, there is no requirement for input from any other test result to test positively for HTLV-I and/or HTLV-II.

Use of such a tax test for widespread blood screening has many unexpected advantages over use of the existing blood screening test based on antibodies to structural proteins of the HTLV virus. Not only will the tax test be positive for virtually every individual who tests positively in the standard HTLV test, but one also will discern very important positives which would have tested negative with the conventional HTLV test. Blood which tests tax positive but structural protein negative is particularly harmful as it has been found that recipients of such blood sera convert to tax positive and the tax protein alone may cause health problems. Thus, an important screening test, i.e., that for structural proteins of HTLV, can be eliminated and substituted with the test of the present invention, which will not only test positive when the blood would have tested positive for the standard HTLV test, but will also find another factor which is not found in the standard HTLV test, but for which it is very important to screen out of blood intended for transfusions.

It has now been found that the transforming/transactivating component of the HTLV-I and HTLV-II virus is the tax sequence and its gene product, p40Tax (reviewed in Centers for Disease Control and Prevention, 1988). Currently, the presence of this component is not tested in blood used for transfusion. However, it was reported several years ago that patients with mycosis fungoides, a skin lymphoma, harbor HTLV-I Tax in their circulating and skin-infiltrating lymphocytes (Zucker-Franklin et al, 1991; Pancake et al; 1995; Khan et al, 1996) while being serologically HTLV-I/II negative. These patients, as well as a high proportion of their healthy relatives, have antibodies to the p40Tax protein (Pancake et al, 1995; Pancake et al, 1996b; Zucker-Franklin et al, 1997a). Since one of these healthy relatives admitted to being a frequent blood donor, a study of blood donors who tested HTLV-I/II serologically negative was initiated. It was found that about 8% of such donors harbor HTLV-I tax sequences in their lymphocytes and have antibodies to the p40Tax protein (Zucker-Franklin, 1997b; Zucker-Franklin et al, 1998).

According to recent reports which give methods and further information regarding the prevalence and transmission of Tax alone, it has been found that Tax alone (without the presence of the complete virus) is taken up by, and is able to immortalize cells in vitro, and that it causes lymphomas and fibromas in Tax transgenic mice (Benvenisty et al, 1992; Nerenberge et al, 1987).

The methods which enabled the present inventors to detect Tax in cells of HTLV seronegative individuals and the reasons some investigators failed to identify "Tax only" positive carriers have been published in detail (Nishioka, 1996; Terada et al, 1994; Sumida et al, 1994; Marriette et al, 1993). The present invention provides a method for rapidly and reliably testing for the presence of HTLV-I and/or HTLV-II in specified populations. This is particularly important for screening potential blood donors and pregnant women who are considering nursing their babies.

Lane 1 PBMC from a HTLV Tax-negative volunteer

Lane 2 HTLV-I-infected cell line, C91PL

Lanes 3–8 PBMC from six different healthy blood donors

Figure 1:
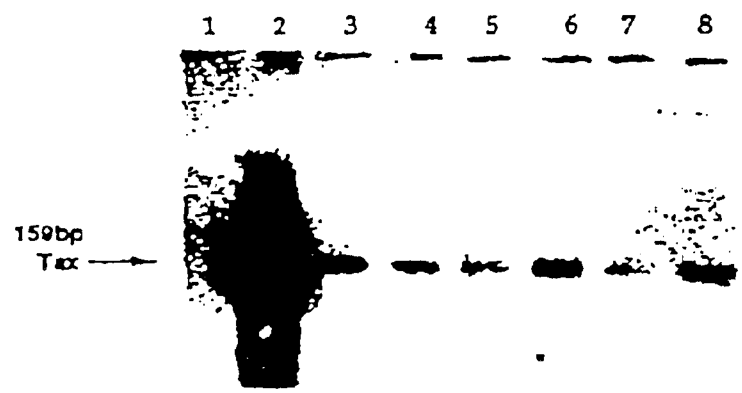
FIG. 1 shows Southern blot detection of HTLV Tax proviral DNA sequences amplified by PCR in lysates of PBMC from HTLV seronegative blood donors. Primers SK43 and SK44 were used in the PCR and digoxigenin-tailed probe SK45 for hybridization. The sources of PCR targets are as follows.
Figure 2:
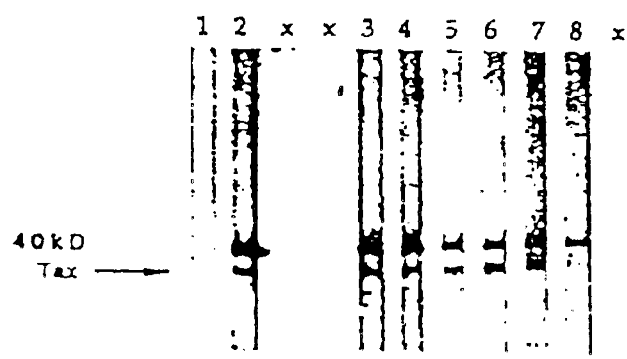
Figure 7A:
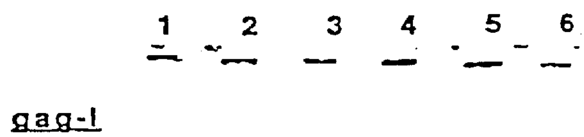
Figure 7B:
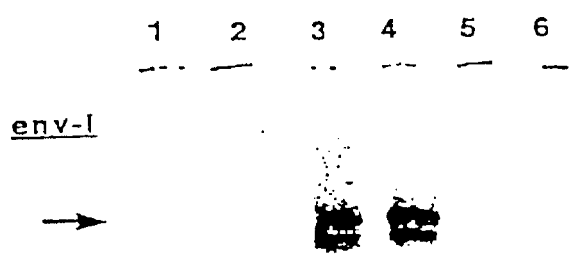
Figure 7C:
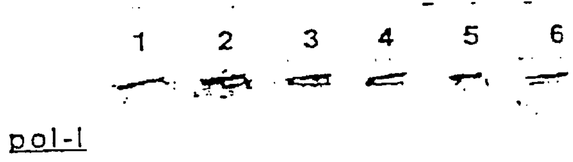
Figure 7D:
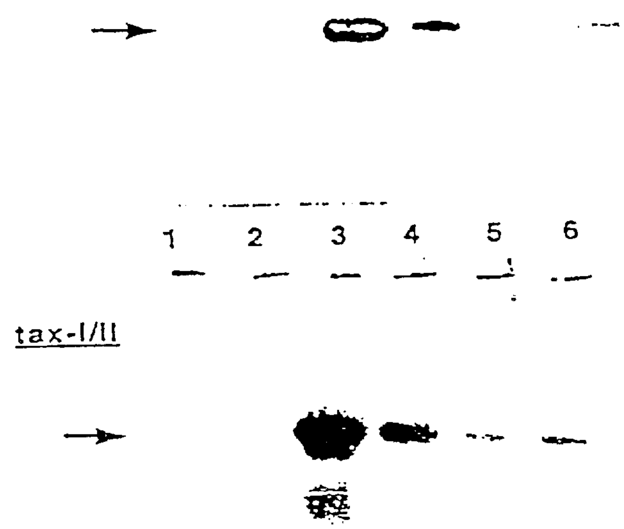

FIG. 2 shows Western blot detection of HTLV antibodies to p40Tax in sera from the same individuals whose amplified tax sequences are shown in the Southern blot in FIG. 1, using recombinant full-length p40Tax antigen. Bound antibody was detected using goat anti-human IgA+IgG+IgM, heavy+light chains, conjugated with alkaline phosphatase. The upper band is uncleaved GST-Tax and the lower band, –40 Tax only.

Sources of plasma were as follows:

Lane 1 HTLV tax sequence and antibody-negative volunteer

Lane 2 HTLV-I infected TSP/HAM patient

Lanes 3–8 Six different healthy blood donors/volunteers x no sample added

FIGS. 3A and 3B show HTLV-I and HTLV-II like tax proviral sequences detected in PBMC lysates. FIG. 3A shows representative HTLV-I tax sequence (Donors) detected in PBMC of fourteen blood donors and six other healthy volunteers. FIG. 3B shows HTLV-II-like tax proviral sequences (I and II) detected in PBMC of two volunteers. The tax sequences for prototypic HTLV-I SEQ ID NO: 1 are those published by Seiki et al, *Proc. Natl. Acad. Sci.* USA 80:3618–3622 (1983), and those for prototypic HTLV-II, SEQ ID NO: 2, by Shimotohno et al, *Proc. Natl. Acad. Sci.* USA 82:3101–3105 (1985). In each case the sequence lines indicated as HTLV-I, SEQ ID NO: 1, is the prototypic sequence from Seiki, and the lines labeled HTLV-II, SEQ ID NO: 2, is the prototypic sequence from Shimotohno. The data for FIG. 3 were published in Zucker-Franklin and Pancake, *Clinical and Diagnostic Laboratory Immunology* 5:831–835, 1998.

FIG. 4 shows the appearance of hypopigmented patches on the patient's skin.

Figures 5A, 5B, 5C, 5D:
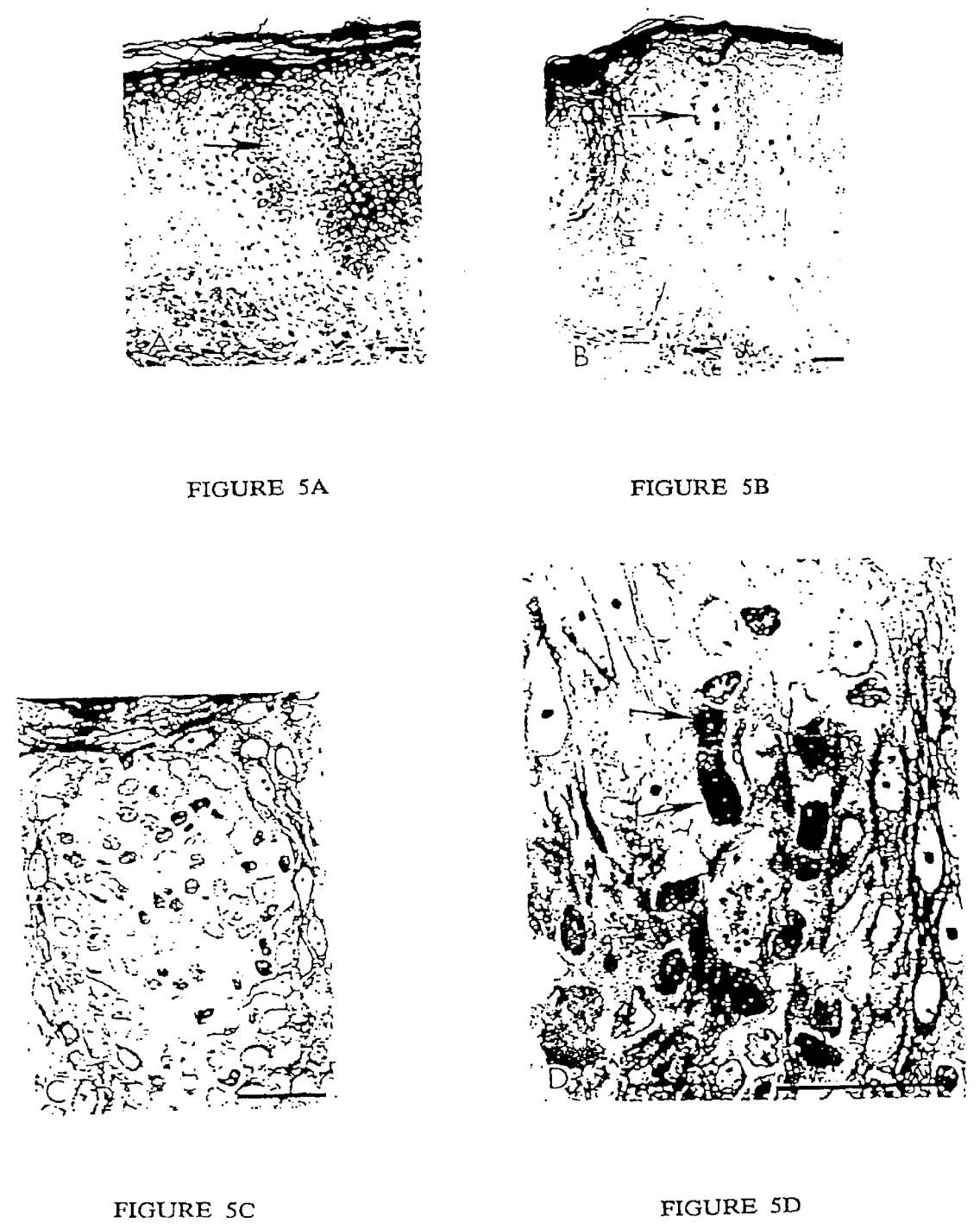

FIGS. 5A–5D show light microscopy of plastic-embedded skin biopsy taken from a hypopigmented area. FIG. 5A illustrates a typical Pautrier micro-abscess in the epidermis. This is shown at a higher magnification in FIG. 5C to delineate infiltrating mononuclear cells to better advantage. FIG. 5B shows a smaller cluster of lymphocytes within the epidermis. However, when the cells indicated by the arrow are seen at higher magnification, as in FIG. 5D, their markedly convoluted nuclei are evident. Also note the dearth of melanosomes in the keratinocytes of this very dark-skinned patient.

Figure 6A:
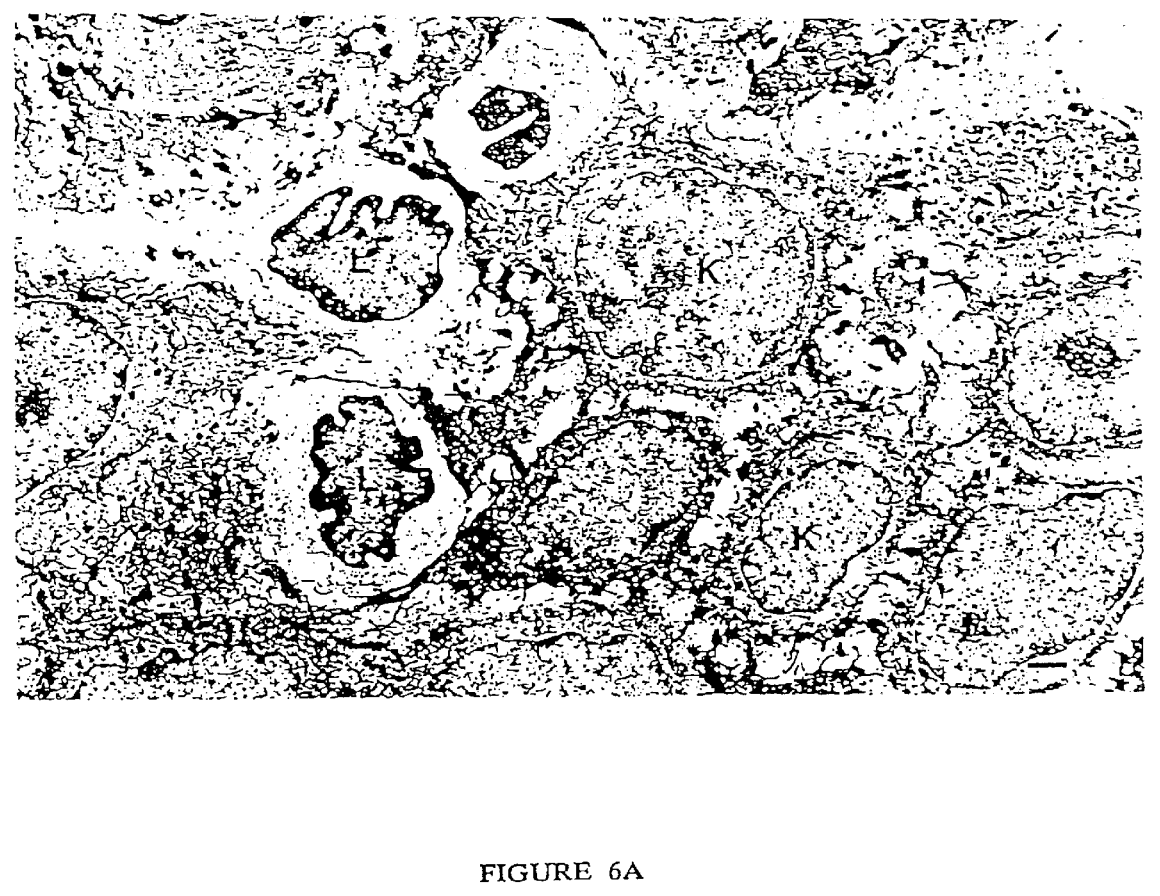

FIG. 6A is an electron photomicrograph of a section through the epidermis showing so-called "flower" cells (L) between sheets of "basket-weave" keratinocytes (K). Note that the keratinocytes contain only a few melanosomes. Magnification×5700; scale bar=1 micron.

Figure 6B:
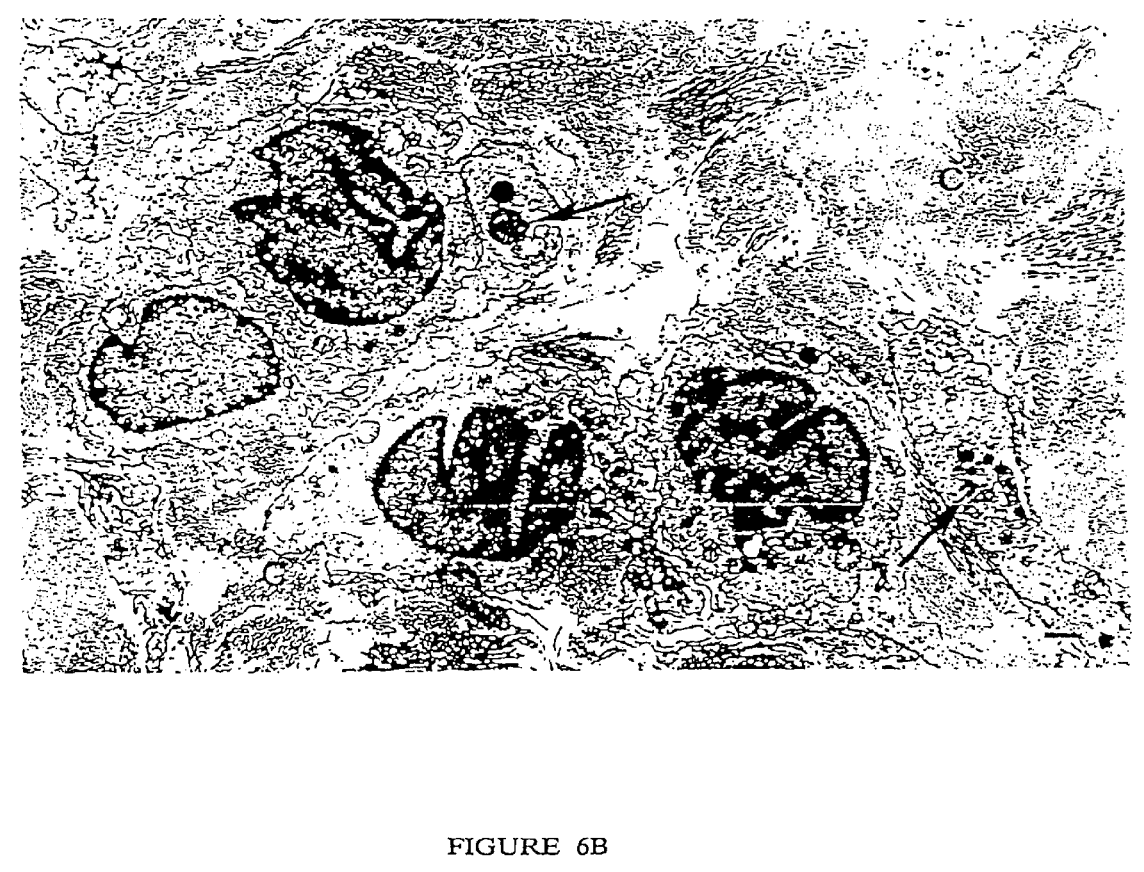

FIG. 6B is an electron photomicrograph of a section through the dermis. Note the infiltrating lymphocytes with highly convoluted nuclei, (C), bundles of collagen fibrils. Arrows indicate a rare cell contains clusters of melanosomes. Magnification is 5700, scale bar=1 micron.

FIGS. 7A–7D show Southern blot hybridization of HTLV-I proviral DNA sequences amplified from whole cell lysates by PCR. Panel A is gag; Panel B is env; Panel C is pol; Panel D is tax. In each panel, Lane 1 is reagent control; Lane 2 is lysate of PBMC from a known negative control; Lane 3 is lysate of HTLV-I-infected C91PL cells; Lane 4 is lysate of PBMC from the patient's mother; Lane 5 is the lysate of PBMC from the patient; and Lane 6 is lysate of PBMC from the patient's brother.

While the cells of the patient's mother harbored all four sequences (Lane 4 in the panels) as did the HTLV-I-infected cell line (Lane 3), PBMC from the patient and his brother had only pol and tax sequences (Lanes 5 and 6).

FIG. 8 shows HTLV-I tax proviral sequences detected by PCR/Southern analysis of PBMC lysates from the mycosis fungoides patient and his mother. The published tax sequences for prototypic HTLV-I (SEQ ID NO:1) and -II (SEQ ID NO:2) are shown (Seiki et al, 1983; Shimotohno et al, 1985). The dashed lines indicate sequence identity with the prototypic HTLV-I sequence (SEQ ID NO:1).

Figure 9:
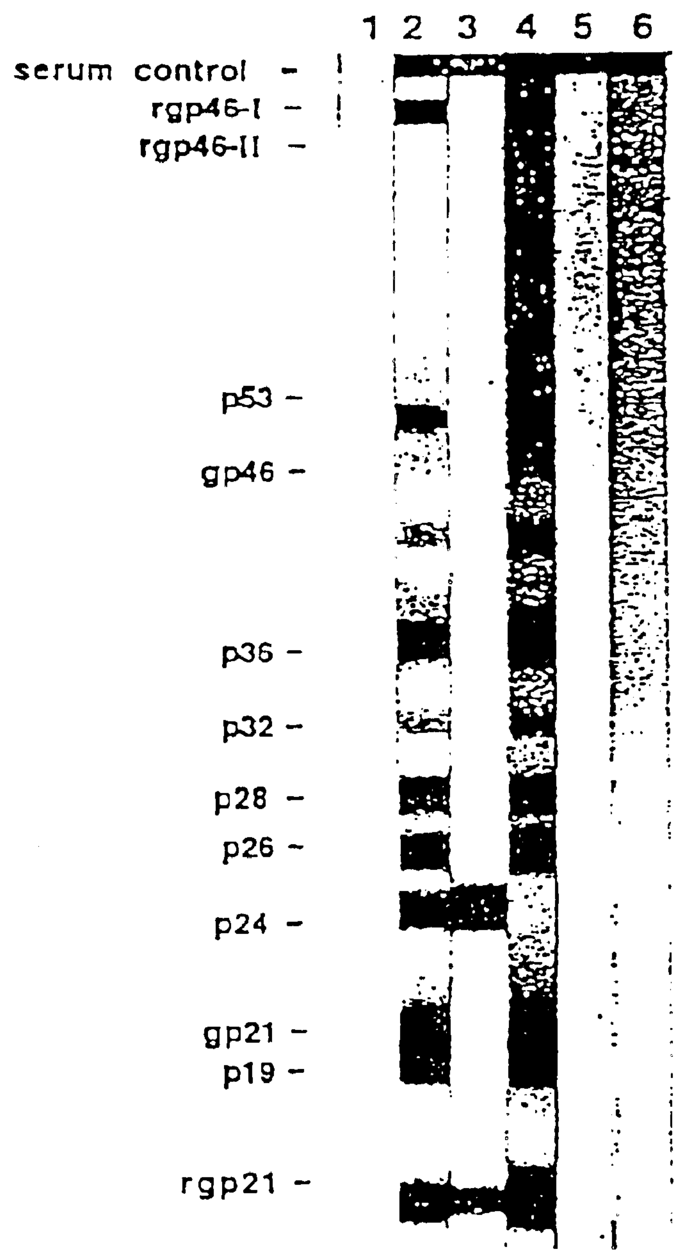

FIG. 9 shows Western blot detection of HTLV-I/II antibodies using the Diagnostic Biotechnology kit HTLV Blot 2.3 from Cellular Products. Positive and negative control sera were supplied in the kit. Sera containing HTLV-I antibodies are distinguished from those seropositive for HTLV-II by the use of recombinant type-specific, Env-related glycoproteins rgp46-I and rgp46-II.

The sources of the specimens are as follows:

Lane 1 negative control

Lane 2 HTLV-I positive control

Lane 3 HTLV-II positive control

Lane 4 mother of the patient

Lane 5 patient

Lane 6 brother of the patient

Figure 10:
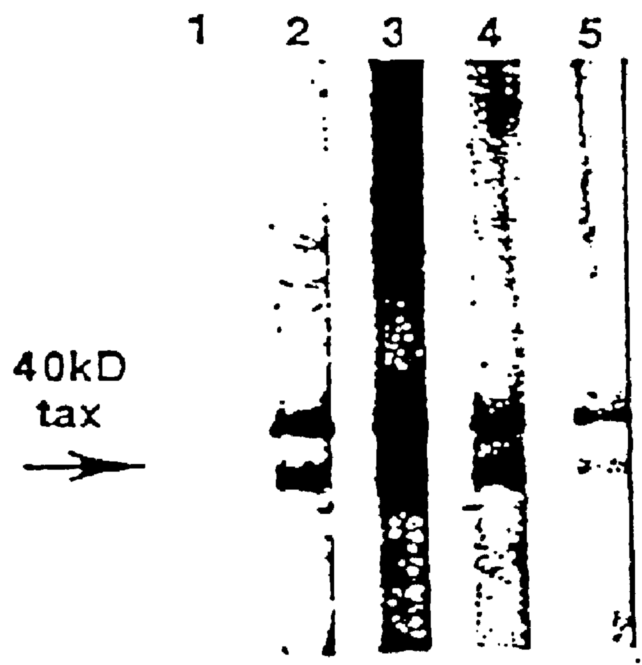

FIG. 10 shows Western blot detection of HTLV p40Tax antibodies. Recombinant full-length p40Tax antigen was prepared by PCR amplification, cloning and expression of p40Tax-coding proviral DNA sequences from the HTLV-I-infected cell line, C91PL. Bound antibodies were detected using goat anti-human IgA+IgM+IgG, heavy+light chains, conjugated with alkaline phosphatase and the alkaline phosphatase substrates NBT and BCIP.

DETAILED DESCRIPTION OF THE INVENTION

The pX region of the HTLV-I genome encodes at least four proteins, including Tax, Rex, p12 and p21 (CDCP, 1988; Gitlin et al, 1993; Yoshida et al, 1985; Franchini, 1995). Interestingly, even in regions of the world where HTLV-I is endemic, it is not unusual to find instances among carriers of the virus, as well as among patients with HTLV-related disease, in whom all viral DNA has been deleted with the exception of the region encoding tax (Korber et al, 1991; Ohshima et al, 1991; Yoshida et al, 1985). The Tax protein is a transcriptional transactivator of its own LTC (Sodroski, 1984). For ease of discussion, the 159 bp proviral DNA encoding a portion of the Tax protein is referred to as the tax sequence in this application. The antigen used to detect Tax antibodies as described herein consists of the entire p40Tax protein.

In HTLV-I endemic regions, the presence of antibodies to the Tax protein has been correlated strongly with both vertical (Sawada et al, 1989) and sexual (Chen et al, 1991) transmission of the virus. Equally intriguing are reports from Japan that 1.5% of healthy HTLV-I carriers and 8.5% of patients with ATLL have antibodies to Tax without having detectable antibodies to the structural proteins of the virus (Shioiri et al, 1993). This phenomenon does not seem to be unusual in endemic regions (Korber et al, 1991; Okayama et al, 1991; Kamihira et al, 1989) and pertains to studies conducted by the present inventors on patients with mycosis fungoides (Pancake et al, 1995; Pancake et al, 1996b).

It was also found that a recently studied nine-year-old patient, with mycosis fungoides whose skin biopsy and PBMC harbored HTLV-I Tax, had antibodies to p40Tax, while being negative for coding sequences and antibodies of the HTLV-I structural proteins. The same pertained to his healthy younger brother, whereas the mother was a carrier, serologically positive for HTLV-I, and had no deleted sequences (Hall et al, 1996).

Unfortunately, many of the early reports on the subject of HTLV-I transmission did not include biomolecular analyses, making it difficult to deduce whether individuals with "Tax only" antibodies also harbored proviral DNA. However, it now suggests that a substantial number of healthy American blood donors have DNA sequences homologous to the HTLV-I tax sequence in their blood mononuclear cells, and that practically all of these individuals also have antibodies to the p40Tax without being serologically positive for antibodies to the structural proteins of the virus.

Since, to date, Tax has not been found in the human genome, it seems warranted to conclude that the "Tax only" state reflects an infection with HTLV-I or a very closely related virus, and that this may be more common in the United States than previously believed.

Ideally, tax sequences detected by the polymerase chain reaction (PCR) and determination of antibodies to p40Tax are the most fool-proof approach to ascertaining the presence of HTLV-I. However, PCR methodology may not be suitable for large-scale testing necessary in many blood banks. Therefore, a reasonable alternative is testing for Tax antibody. In fact, since individuals who are serologically positive for antibodies to HTLV-I/II also have antibodies to the p40Tax protein, the currently used test kits can be replaced by one kit containing only the p40Tax antigen.

Data were obtained from 250 specimens, comprising samples obtained from 20 volunteer blood bank donors, who had no risk factors, as defined by the United Stated blood banking community, and 40 additional volunteers recruited from among NYUMC staff.

In order to substantiate the assumption that healthy individuals in non-endemic regions may carry proviral sequences homologous to HTLV-I Tax, without having antibodies to the structural proteins of the virus, the tax sequences amplified from PBMC lysates of 22 of these "Tax only" positive healthy individuals were subjected to nucleotide sequence analysis.

Furthermore, to explore whether "Tax only" positivity has any clinical relevance, a study was initiated on specimens obtained from patients with rheumatoid arthritis. This particular autoimmune disease was chosen initially because mice transgenic for HTLV-I Tax develop clinical and pathologic manifestations indistinguishable from those of rheumatoid arthritis in humans (Iwakura et al, 1991; Iwakura et al, 1995). Preliminary data suggest that the "Tax only" state is more common in patients with rheumatoid arthritis than among healthy blood donors.

MATERIALS AND METHODS

Specimens

Heparinized blood was collected with informed consent and approval by the Institutional Review Board from 250 healthy adults who had no risk factors which would have disqualified them from donating blood for transfusion. All donors tested negative for antibodies to HTLV-I/II by ELISA and Western blot tests performed at the New York Blood Center and/or in the inventors' laboratory. Among the 250 were 210 who, independent of this study, donated a unit of blood at the New York University Medical Center Blood Bank, and 40 healthy volunteers who were recruited by advertisement from among the personnel at NYUMC. Twenty-six of the non-blood bank donors were Caucasian Americans, 3 were African Americans, 3 were African Caribbeans. The remaining eight consisted of one Black Nigerian, two Koreans, one Japanese from Taiwan, and four Indian/Pakistanis.

Blood samples were also obtained from 57 patients diagnosed to have rheumatoid arthritis according to criteria established by the American Rheumatism Association (Arnett et al, 1988). The rheumatoid arthritis patients were referred by rheumatologists affiliated with NYUMC.

Blood samples were fractionated into plasma and mononuclear cells (PBMC) by Ficoll/Hypaque gradient centrifugation using conventional techniques (Zucker-Franklin et al, 1974). Sterile techniques were strictly adhered to during all procedures, and each specimen was handled at a different site and usually on different days.

Detection of HTLV-I/II Proviral DNA Sequences in PBMC

Preparation of Cell Lysates and PCR Amplification

Whole cell lysates were prepared from approximately $10^5$ mononuclear cells obtained from peripheral blood (PBMC) as described (Pancake et al, 1995). Briefly, cells were lysed in autoclave-sterilized distilled water by sonication and boiling, followed by incubation for one hour at 55° C. in the presence of 2 μg of proteinase K per sample. The samples were then boiled to inactivate the protease and subjected to 30 cycles of PCR amplification (1' at 94° C., 1' at 55° C. and 1.5' at 72° C. per cycle, followed by a final incubation for 10' at 72° C., in the buffer and concentrations of dNTO's described. The final sample reaction volume of 80 μl includes 40 pmol of primers (see below) and 4U of Taq polymerase (Perkin Elmer, Foster City, Calif.) (Pancake et al, 1995; Zucker-Franklin et al, 1997a, Hall et al, 1991; Kwok et al, 1988). PCR was conducted in the Perkin Elmer Model 480 Thermal Cycler. Positive and negative control cells for the PCR consisted of lysates of the prototypic HTLV-I- and II-infected cell lines, C91PL (HTLV-I) (Popovic et al, 1983) and MoT(HTLV-II (Saxon et al, 1978), respectively, in addition to PBMC from HTLV-I/II gag, pol, env and tax PCR sequence-negative healthy volunteers.

Southern Analysis

PCR products were resolved through 4% agarose gels in the presence of ethidium bromide, followed by denaturation, neutralization and overnight transfer of DNA to nylon membranes, as described before (Pancake et al, 1995). DNA was cross-linked to the membranes by incubation for one hour at 80° C., followed by prehybridization and hybridization at 43° C. for two hours and overnight, respectively, using the probes listed below, 3'-tailed with digoxigenin. Detection of bound probes entailed use of Fab' fragments of antibodies to digoxigenin, conjugated with alkaline phosphatase and the alkaline phosphatase substrates, 4-nitroblue tetrazolium (NBT) and 5-bromo-4-chloro-3-indolyl phosphate (BCIP). The reagents for 3'-tailing probes with digoxigenin and detection of bound probe were obtained from Boehringer-Mannheim (Indianapolis, Ind.).

Primers and Probes

The primers and probes used were HTLV gag-I and env-I primers and probes (Hall et al, 1991); pol-I/II primers, SK110, SK111 and probes SK 112 (pol-I), Sk188 (pol-II) and tax-I/II primers, SK43, SK44 and probe, SK45 (Kwok et al, 1988). The sequences and HTLV genome locations of additional gag primers and probes were published (Zucker-Franklin et al, 1997a) gag-I/II: sense and antisense primers: (BP4)5'-CCCATCTTACGTTCCCTAGC-3' (SEQ ID NO:5) (HTLV-I:1690–1709; HTLV-II:1713–1732), (BP5) 5'GGATCTTGACATAGGGGGCA-3' (SEQ ID NO:6) (HTLV-I:1939–1958; HTLV-II:1962–1981), and probe (BP6) 5'-ACATGGAGTCGGGACTGCACCCAGCC-3' (SEQ ID NO:7) (HTLV-I:1890–1919; HTLV-II:1913–1942). The gag-II primers included: (BP1)5'-TCACGGGTTTCCCAACT-3' (SEQ ID NO:8) (HTLV-II:817–833), (BP2)5'-TGTCAAAAATCAAGTCTCCCCTAGCC-3' (SEQ ID NO:9) (HTLV-II:1067–1092). The genome sequences and locations reported are those of Seiki et al (1983) for HTLV-I and Shimotohno et al (1985) for HTLV-II. The conditions and temperature for PCR amplification and hybridization using these primers and probes were the same as those for HTLV Tax (SK43, SK44, SK45) and pol (SK110, SK111, SK112) described previously (Pancake et al, 1995).

Detection of Antibodies to HTLV p40Tax

Preparation of Tax Antigen

The proviral DNA sequences encoding the full-length tax-I open reading frame were amplified by PCR from the prototypic HTLV-I-infected cell line, C91PL (Popovic et al, 1983) as described in detail by Pancake et al (1996b). The amplified sequences were cloned into the glutathione S-transferase (GST) fusion protein expression vector, pGEX-2T and p40Tax antigens were prepared by expression of recombinant GST-p40Tax proteins in *E. coli*, BL21 cells, followed by isolation of the recombinant GST-p40Tax protein by chromatography using glutathione cross-linked to Sepharose 4B (Pharmacia Biotech, Piscataway, N.J.) and release of the p40Tax protein by thrombin cleavage.

Western Blot Assay

Thrombin-cleaved full-length p40Tax antigen was resolved through preparative 8.5% SDS-polyacrylamide gels, followed by electrophoretic transfer to nitrocellulose. After overnight blocking in 100 mM Tris-HCl, pH 7.5, 150 mM NaCl containing 2% Blocking Reagent (Boehringer-Mannheim), blots were exposed to test and control plasmas, using the BioRad Mini-Protean II multiscreen apparatus as a template. As reported elsewhere (Pancake et al, 1996b), the majority of plasmas were diluted 1:10, as it had previously been shown that higher dilutions often failed to detect the antibody. After incubation of blots in the presence of the test plasmas for one hour at room temperature, blots were washed extensively followed by incubation with secondary antibody (goat-anti-human IgA+IgG+IgM, H, +L chains, conjugated with alkaline phosphatase; Pierce Chemical Co., Rockford, Ill.) and the alkaline phosphatase substrates NBT and BCIP (Boehringer-Mannheim). HTLV-positive and negative human sera were included as controls in each assay.

Sequence Analysis

Tax sequences amplified from specimens from 22 individuals were subjected to oligonucleotide sequence analysis. All specimens chosen for sequence analysis were derived from individuals who also had antibodies to the tax protein.

Whole cell lysates prepared from Ficoll/Hypaque gradient-fractionated PBMC as described above were subjected to two rounds of PCR amplification, each consisting of 30 cycles of 1' at 94° C., 1' at 55° C., and 1.5' at 72° C., followed by a final 10' incubation at 72° C., under the PCR conditions described above. In PCR 1, primers SK43/SK44 were used.

The second PCR was initiated by the transfer of 2 $\mu$l of the PCR products generated in PCR 1, to a final PCR 2 reaction volume of 80 $\mu$l per sample. The primers used in PCR 2 consisted of the sense and antisense primers: 9376 (5'-CGTGT TTGGAGACTGTGTAC-3') (SEQ ID NO:10) and 9377 (5'-CATCGATGGGGTCCCAGGTG-3') (SEQ ID NO:11). The underlined sequences in primers 9376 and 9377 correspond to the 5 base 3' ends of SK43 and SK44, respectively. Oligonucleotide HTLV gag, pol, env and tax primers and probes were synthesized in the oligonucleotides Synthesis and Sequencing Facility at NYUM.

Positive and negative controls for PCR reactions included: lysates of the HTLV-I-infected cell line, C91PL (Popovic et al, 1983), the HTLV-II-infected cell line, MoT (Saxon et al, 1978), and known HTLV-I/II PCR-negative PBMC, respectively. The products from PCR 1 and 2 were resoled through ethidium bromide-stained 4% agarose gels. The remaining DNA amplification products that gave rise to visible bands in gels for the PCR 2 samples were subsequently isolated using reagents and columns supplied in the QIAquick Spin PCR Purification kit obtained from QIAGEN, Inc. (Chatsworth, Calif.), and sequenced directly by the NYUMC Sequencing Facility, using primers 9376 and 9377. Sequences detected in samples were compared with those published for HTLV-I and -II (Seiki et al, 1983; Shimotohno et al, 1985; Lee et al, 1993; Hall et al, 1992; Eiraku et al, 1996; Kitajima et al, 1991) for the 128 bp tax proviral DNA sequence being analyzed. HTLV-I and -II differ in this region by 16 base pairs.

Detection of HTLV Proviral DNA Sequences and Antibodies to p40Tax

Because of the questionable nature of data based solely on the polymerase chain reaction (PCR), reported here as positive were only those individuals who had both tax proviral sequences and antibodies to the Tax protein.

Among the 210 blood bank donors, whose blood was found acceptable for transfusion purposes, 18, i.e., 8.6% were tax sequence as well as Tax antibody-positive, which is consistent with published preliminary studies (Zucker-Franklin et al, 1997b). As for the 40 non-blood bank donors, five were shown to have tax-I sequences and two had tax-II sequences. All seen had antibodies to p40Tax. The apparent difference between the two groups of healthy donors is not statistically significant. Neither PMBC from the blood bank nor from the other donors was found to contain HTLV gag-I, gag-II, gag- I/II, pol-I, pol-II or env-I sequences. A representative Southern blot of tax proviral sequences detected in six different donors is shown in FIG. 1 and representative Western blot data for the same tax sequence-positive donors represented in FIG. 1 are presented in FIG. 2. None of the 250 individuals was seropositive or exhibited antibodies to the viral structure proteins Gag and Env, which were tested routinely at the New York Blood Bank.

The tax proviral DNA sequences amplified in PBMC lysates obtained from 22 tax-positive healthy individuals are shown in FIG. 3. The HTLV tax sequence detected in 20 of these donors proved to be homologous to prototypic HTLV-I tax (FIG. 3, panel A), whereas sequences from two individuals had had several bases in common with HTLV-II (panel B). It should be pointed out that in this region prototypic taxI and II differ in sequence by 16 base pairs (Seiki et al, 1983; Shimotohno, 1985; Lee et al, 1993; Hall et al, 1992; Eiraku et al, 1996; Kitajima et al, 1991). Both of the individuals, whose cells harbored HTVL-II-like, rather than HTLV-I Tax sequences, were of Indian/Pakistani origin.

Observations on Specimens from Patients with Rheumatoid Arthritis

To date, paired PBMC and plasmas have been obtained from only 57 patients with rheumatoid arthritis. Fifteen of the 57 (26.3%) were positive for both tax sequences and antibodies to p40Tax. None of the rheumatoid arthritis patients harbored gag, pol, or env sequences, and all were HTLV-I/II seronegative when tested by routine analyses. On the basis of these preliminary data, it appears that the "Tax only" state is three times more prevalent among patients with rheumatoid arthritis than among the health blood donor population ($p<0.0001$).

While the tax sequence found in the PBMC of 20 of 22 donors was characteristic of HTLV-I, the cells of two donors harbored tax sequences resembling HTLV-II. Further investigation revealed that both of these donors were Pakistani. Although the prevalence of HTLV-I/II infection in India/Pakistan has not been established, it is known that HTLV-II is endemic in Southeast Asia as well as among Indian populations in both North and South America (Hall et alm 1996).

While the transforming ability of HTLV-I is common knowledge, its role in the development of autoimmunity is less well recognized. In non-endemic regions of the world, such as the United States, few clinicians encounter patients with TSP/HAM. Therefore, as a rule, little thought is given to the fact that the latter condition is not neoplastic. It is also not widely known that Tax transactivates numerous cellular genes, that it is involved in the activation of many cytokines, and that, via NFkB, it dysregulates the cellular as well as humoral immune response (reviewed in Yoshida, 1994; Gitlin et al, 1993; Buckle et al, 1996). In HTLV-I endemic regions, many autoimmune conditions, such as Sjögren's Syndrome (Sumida et al, 1994; Nishioka et al, 1996; McCallum et al, 1997), HTLV-related arthropathy (Nishioka, 1996; Eguchi et al, 1996) and idiopathic uveitis (Mochizuki et al,. 1992) are considerably more prevalent among carriers of HTLV-I than among cohorts that are serologically negative for antibodies to the virus. For instance, on the Kyushu island of Japan, idiopathic uveitis is three times more prevalent among HTLV-I carriers than in the uninfected population (Eguchi et al, 1996). Another Japanese study showed a 20% incidence of rheumatoid arthropathy in otherwise healthy HTLV-I carriers, whereas this condition was only found in 4% of 19,796 HTLV-I negative blood donors tested in the same geographic region.

Because mice transgenic for Tax happen to serve as good animal models for rheumatoid arthritis (Iwakura et al, 1991; Iwakura et al, 1995), a possible association of Tax positivity with autoimmune diseases was investigated by studying patients with rheumatoid arthritis. On the basis of preliminary observations on the first 107 patients, it appeared that the "Tax only" state is three times higher in rheumatoid arthritis patients than among healthy blood donors. Tax sequences have also been identified by in situ hybridization in labial epithelial cells of some patients with Sjögren's Syndrome who were seronegative for HTLV-I/II (Mariette, 1993).

It has become generally recognized that autoimmune diseases. such as rheumatoid arthritis, may have multiple etiologies. Concepts of antigenic cross-reactivity, "molecular mimicry", and "epitope spreading" have been reviewed (McCallum et al, 1997; von Herrath et al, 1996; Vanderlught et al, 1996). A large variety of foreign antigens can elicit cellular and humoral immune responses, which affect self antigens, particularly in the context of a conducive histocompatibility setting. HTLV-I Tax may have to be added to the list of such agents.

Tax Associated with Mycosis Fungoides

The cutaneous T cell lymphoma, mycosis fungoides, is characterized by proliferation of atypical lymphocytes that preferentially home to the skin. Patients are usually middle-aged and present with erythematous patches and plaques. Although it is often indolent, the disease may progress to a tumor state and involve viscera.

However, a seven-year-old Black male, born in Grenada, presented with a three-year history of slowly developing, hypopigmented patches scattered over his buttocks, legs and arms involving approximately 20% of his body surface. He was serologically negative for antibodies to HTLV-I/II. The young age of this patient, the hypopigmentation of his lesions, his origin from a region of the world where HTLV-I is endemic, and previous studies showing an association of HTLV-I tax with mycosis fungoides (Pancake et al, 1995; Khan et al, 1996) prompted investigation as to whether the patient and/or his first degree relatives were infected with this virus. While the patient's healthy mother provided to be a carrier of HTLV-I, with antibodies to the virus when tested by routine serologic methods, the patient, like other patients with mycosis fungoides, as well as his healthy younger brother, harbored only deleted HTLV-I proviral sequences.

Blood Specimens

Sera and blood mononuclear cells I(PMBC) were fractionated from heparinized whole blood of the patient, his mother and his brother by Ficoll/Hypaque gradient centrifugation by conventional means (Zucker-Franklin et al, 1974) Sézary cell counts were carried out on sectioned, embedded cells on the light microscopic and ultrastructural level using criteria reported in detail elsewhere (Zucker-Franklin et al, 1974; Myrie et al, 1980).

Detection of HTLV Proviral DNA Sequences

The procedures used to prepare whole cell lysates of PBMC, in addition to the conditions for PCR and Southern analysis using digoxigenin-tailed probes, have been previously reported (Pancake et al, 1995; Pancake et al, 1996a). Briefly, $1–2\times10^5$ PBMC were lysed by boiling for 8–10 minutes in 55 μl autoclave-sterilized distilled water, followed by incubation for one hour at 55° C. in the presence of proteinase K (2 μg/sample) and subsequent boiling to inactivate the protease. Following preparation of lysates, 80 μl final sample reaction volumes containing 40 pmol of each primer, 2.5 mM $MgCl_2$, 1×PCR Buffer II, 200 mM each of dATP, dCTP, dGTP, and dTTP, and 4U of Taq polymerase (Perkin Elmer, Foster City, Calif.), overlaid with 50 μl of autoclaved mineral oil, were subjected to 30 cycles of PCR amplification consisting of 1' at 94° C., 1' at 55° C., and 1.5' at 72° C. per cycle and a final 10' incubation at 72° C. in a Perkin-Elmer/Applied Biosystems Model 480 Thermal Cycler. PCR samples were resolved through 4% ethidium bromide-containing agarose gels, followed by denaturation in 0.5 M NaCl and neutralization in 1.5 M Tris-HCl (pH 7.5) for 15 minutes each, and Southern transfer to nylon membranes The membranes were blocked and exposed to the appropriate digoxigenin-tailed HTLV probe and detection of bound probe was carried out using Fab' fragments of antibodies to digoxigenin, conjugated with alkaline phosphatase. Reagents and procedures for 3'-tailing probes with digoxigenin and detection of bound probe were obtained from Boehringer-Mannheim (Indianapolis, Ind.) and used by the present inventors as reported previously (Pancake et al, 1995; Pancake et al, 1996a). The primers and probes used in this study included the HTLV gag-I and env-I primers and probes (Kwok et al, 1988). Oligonucleotide HTLV gag, pol, env and tax primers and probes were synthesized in the Oligonucleotide Synthesis and Sequencing Facility at NYUMC. The conditions and temperatures for PCR amplification and hybridization using these primers and probes were described previously (Pancake et al, 1995; Zucker-Franklin et al, 1997a). Proviral sequences were also analyzed in lysates prepared from the patient's skin biopsy.

Oligonucleotide Sequence Analysis of the Tax Sequences Detected in PBMC Lysates

Tax sequences amplified in specimens from the patient and his mother were subjected to oligonucleotide sequence analysis. Whole cell lysates prepared from Ficoll/Hypaque gradient-fractionated PBMC were subjected to two rounds of PCR amplification, each consisting of 30 cycles of 1' at 94° C., 1' at 55° C., and 1.5' at 72° C., followed by a final 10' incubation at 72° C. In PCR 1, primers SK43/SK44 were used. The second PCR was initiated by the transfer of 2 μl of the PCR products generated in PCR 1 to a final PCR 2 reaction volume of 80 μl per sample. The primers used in PCR 2 consisted of the sense and antisense primers: 9376 (5'-CGTGTTTGGAGACTGTGTAC-3') (SEQ ID NO:10) and 9377 (5'-CATCGATGGGGTCCCAGGTG-3') (SEQ ID NO:11). The underlined sequences in primers 9376 and 9377 correspond to the 5 base 3' ends of SK43 and SK44, respectively. The products from PCR 1 and 2 were resolved through ethidium bromide-containing 4% agarose gels. The remaining DNA amplification products that gave rise to visible bands in gels for the PCR 2 samples were subsequently isolated using reagents and columns supplied in the QIAquick Spin PCR Purification kit obtained from QIAGEN, Inc., (Chatsworth, Calif.) and sequenced directly by the NYUMC Sequencing Facility, using primers 9376 and 9377. Sequences detected in samples were compared with those published for HTLV-I and HTLV-II (Seiki et al, 1983; Shimotohno et al, 1985) for the 128 base pair tax proviral DNA sequence being analyzed. HTLV-I and -II differ in this region by 16 base pairs.

Detection of Antibodies to HTLV-I/II

Sera were diluted 1:100 in tests for antibodies to HTLV-I and -II using the Diagnostic Biotechnology HTLV-Blot 2.3 Western blot assay, obtained from Cellular Products (Buffalo, N.Y.) as described in Zucker-Franklin et al (1997a). This test permits distinguishing between individuals who are seropositive for HTLV-I from those with antibodies to HTLV-II. The sera were also tested by ELISA and Western blot assays for antibodies to HTLV-I/II at the New York Blood Center.

Detection of Antibodies to HTLV-I p40Tax

Antibodies to HTLV p40Tax were determined by Western blot assay using recombinant full-length p40Tax-I antigen (Pancake et al, 1996b). The HTLV-I p40Tax protein was prepared by cloning PCR-amplified proviral DNA sequences spanning the entire tax open reading frame from the prototypic HTLV-I-infected cell line, C91PL (Popovic et al, 1983) into the glutathione-S-transferase fusion protein expression vector pGEX-2T (Smith et al, 1987). The recombinant GST-p40Tax-I fusion protein was expressed in *E. coli* BL21 cells and purified by chromatography using glutathione linked to Sepharose 4B (Pharmacia Biotech, Piscataway, N.J.) and subsequent thrombin cleavage. Recombinant p40Tax-I protein was resolved through 8.5% preparative polyacrylamide gels, and electrophoretically transferred to nitrocellulose. Sera from test subject and controls were diluted 1:10. The recombinant p40Tax protein was identified in the assays using a polyclonal antiserum raised to recombinant full-length proTax protein expressed in a baculovirus expression system, obtained from the NIH AIDS Research and Reference Reagent Program (Jeang et al, 1987), and through the use of serum from a TSP/HAM patient. The assays were developed using goat anti-human IgA+IgG+IgM and goat anti-rabbit IgG antibodies conjugated with alkaline phosphatase and the alkaline phosphatase substrates NBT and BCIP (Pierce Chemical Co., Rockford, Ill.) as described previously (Pancake et al, 1996b).

Histopathology of the Skin

Representative sections of the skin biopsy viewed by light and electron microscopy exhibited typical Pautrier abscesses (FIG. 5A) and the infiltration of lymphocytes with highly-convoluted nuclei in the dermis as well as in the epidermis (FIGS. 6A and 6B) which are pathogenomic for mycosis fungoides. There appeared to be a dearth of melanosomes in the keratinocytes of this very dark-skinned young patient. Degenerative changes of melanocytes or keratinocytes, described in some reports of hypopigmented mycosis fungoides lesions (Breathnach et al, 1982) were not seen.

Electron Microscopy of Blood Cells

Although no abnormal cells were evident on the patients' routine blood smear, on electron microscopy 24% of his purified lymphocytes were considered to have abnormally convoluted nuclei by ultrastructural criteria defined elsewhere (Zucker-Franklin et al, 1974).

Detection of HTLV-I Proviral DNA Sequences

As anticipated, HTLV-I gag, pol, and env, as well as tax-I/II proviral DNA sequences were detected in lysates of PBMC obtained from the patient's mother. However, only pol-I and tax sequences were found in cell lysates prepared from the patient and his healthy brother (FIG. 7). The same sequences were detected in lysates of the patient's skin biopsy.

Sequence Analysis

The tax sequences detected in the PBMC lysates from both the patient and his mother were homologous to that published for HTLV-I, for the region of tax analyzed, and can be seen in FIG. 8)

Detection of HTLV-I/II Antibodies

The patient's mother was serologically positive for antibodies to HTLV-I (FIG. 9). Here it is evident that the patient's mother had antibodies to numerous structural proteins of the virus, whereas such antibodies could not be detected in the sera of the patient or his healthy brother. On the other hand, all three individuals had antibodies to the proTax protein, which is encoded by the pX region of the virus (FIG. 10).

It has been demonstrated (Pancake et al, 1995; Hall et al, 1991; Ghosh et al, 1994; Manca et al, 1994) that the majority of patients with mycosis fungoides harbor a sequence homologous to HTLV-I Tax in their blood and skin-infiltrating lymphocytes (Khan et al, 1996), like other HTLV-I associated conditions, mycosis fungoides usually develops only late in life. The NYUMC cutaneous lymphoma database, comprise upwards of 600 patients, only nine, including the present case, were under the age of 20. The patient reported here was only seven years old. Although hypopigmentation was the most striking manifestation, which brought this patient to medical attention, a review of the literature suggests that hypopigmentation is not unusual (Sigal et al, 1987; Amichai et al, 1996), albeit not exclusively seen in dark-skinned individuals with this disease (Handfield-Jones et al, 1992; El-Hoshy et al, 1995; Misch et al, 1987; Ratnam et al, 1994; Zackheim et al, 1982; Zackheim et al, 1997). It may also be more common in the younger age group (Lambroza et al, 1995). Indeed, this raises the possibility that in HTLV-I-endemic regions, mycosis fungoides may be under-diagnosed, when it occurs in otherwise healthy children, presenting only with hypopigmented skin lesions.

As to the pathology, apart from the infiltration of the epidermis and dermis with aberrant lymphocytes, which established the diagnosis, there was the expected decrease in melanosomes. However, even ultrastructural analysis did not reveal degenerative changes in the cells normally residing in the skin, which has been reported occasionally (Breathnach et al, 1982; Goldberg et al, 1986). This may explain the patient's excellent response to UVBm which probably affected primarily the infiltrating mononuclear cells. Unfortunately, the patient's circulating lymphocytes still harbor HTLV-I Tax, which makes a complete cure unlikely.

To date, the majority of mycosis fungoides patients studied by the present inventors did not come from regions of the world in which the virus is endemic. Nevertheless, the sequences harbored in their lymphocytes are homologous with HTLV-I Tax and most of them have antibodies to proTax, the gene product of this sequences (Pancake et al, 1995; Pancake et al, 1996b). In addition, studies carried out on some healthy relatives of mycosis fungoides patients showed that they had the same sequence as the patients, as well as antibodies to the proTax protein.

The present case is of particular interest since the patient, as well as his brother, were breast-fed by their mother, who is a healthy carrier of HTLV-I (FIGS. 8–10). It is well recognized that HTLV-I is harbored by mononuclear cells in breast milk and that transmission of the virus occurs via this route in man (Kinoshita et al, 1984) as well as in animals (Hirose et al, 1988; Iwakura et al, 1990). In addition, it is known that deletions of the HTLV-I genome are very common and that the number and extent of such deletions often varies among members of the same family (Kashiwagi et al, 1990; Shiori et al, 1993; Ohshima et al, 1991; Korber et al, 1991).

In the patient reported here, as well as in his brother, only tax and pol sequences were retained (FIG. 7). Both children were serologically negative for antibodies and lacked the coding sequences for the structural proteins of the virus (FIGS. 9 and 7). Careful review of the literature suggests that even when infection with HTLV in young patients with mycosis fungoides is considered, as deduced from statements that serologic screening for antibodies to HTLV-I had been negative (Pancake et al, 1995), biomolecular analyses or appropriate tests to detect antibodies to proTax were usually not performed. Yet it has been well established that deleted retroviruses can be associated with leukemic processes in animals (Wong-Staal et al, 1983), as well as with the development of adult T cell lymphoma in humans (Ohshima et al, 1991; Korber et al, 1991). Retention of Tax is of particular significance because it is known to be instrumental not only in transformation (Nerenberg et al, 1987) but also in the transactivation of numerous cellular genes encoding cytokines and growth factors (Gitlin et al, 1993).

It is not clear why this patient and his brother did not have antibodies to HTLV when they must have been exposed to the whole virus via breast feeding. In this regard, it should be recalled, however, that tolerance to fed antigens, particularly at an early age, is a well characterized phenomenon (Movat, 1987). The absence of antibodies to the structural proteins, Env and Gag, could be explained on this basis. Whether oral administration of an antigen generates an immune response or tolerance appears to depend, in part, on the nature of the antigen (Weiner et al, 1994).

Even maintenance of infection with intact HTLV-I is likely to depend on clonal expansion of infected cells rather than independent proliferation of the virus (Wattel et al, 1996). This may also be applicable to defective HTLV, i.e., the expression of the tax sequence and its gene product, the proTax protein, in cells of the patient and his brother. Apart from having proviral sequences, this patient's PMBC continue to have tax mRNA (Pancake et al, 1996b), making it likely that the proTax protein continues to be synthesized. Therefore, persistence, and with time, an increased burden of Tax-containing cells could be responsible for the generation of antibody to Tax in the absence of antibodies to the structural proteins of the virus.

This strengthens the argument that HTLV-I or a very closely related virus is associated with mycosis fungoides. Perhaps even more important is the message that nonpruritic, hypopigmented skin lesions in a child should alert pediatricians and dermatologists to the possible diagnosis of mycosis fungoides, even if the patient is serologically negative for antibodies to HTLV-I/II as tested by routine methods.

Of particular importance is the fact that one can determine infection by HTLV-I/II solely by testing for the prevalence of the Tax protein of HTLV-I/II.

All references cited herein, including journal articles or abstracts, published or unpublished U.S. or foreign patent applications, issued U.S. or foreign patents, or any other references are entirely incorporated by reference herein, including all data, tables, figures, and text present in the cited references. Additionally, the entire contents of the references cited within the references cited herein are also incorporated by reference in their entirety.

References to known method steps, conventional method steps, known methods or conventional methods is not in any way an admission that any aspect, description, or embodiment of the present invention is disclosed, taught, or suggested in the relevant art.

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . ." and "means for . . .", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same function can be used; and it is intended that such expressions be given their broadest interpretation.

REFERENCES

Amichai et al, *J. Dermatol.* 23:425–426 (1996)

Arnett et al, *Arthr. & Rheum.* 31:315–324 (1988)

Benvenisty et al, *Oncogene* 7:2399–2405 (1992)

Blattner, W. A. *Ann. Int. Med.* 111:4–6 (1989)

Breathnach et al, *Br. J. Dermatol.* 106:643–649 (1982)

Buckle et al, *J. AIDS & Human Retrovir.* 13(Supl):S107–S113 (1996)

Centers for Disease Control and Prevention (CDCP) *Morbid, and Mortal. Wkly Rep.*, 37:736–747 (1988)

Chen et al, *Proc. Natl. Acad. Sci. USA* 88:1182–1186 (1991)

Copeland et al, *J. Immunol.* 137:2945–2951 (1986)

Eguchi et al, *Arthr. & Rheum.* 39:463–466 (1996)

Ehrlich *Blood* 74:1066–1072 (1989)

Eiraku et al, *J. Virol.* 70:1481–1492 (1996)

El-Hoshy et al, *J. Dermatol.* 22:424–427 (1995)

Franchini, G. *Blood* 86:3629–3639 (1995)

Gessain et al, *Lancet* ii:407–410 (1985)

Ghosh et al, *Blood* 84:2663–2671 (1994)

Gitlin et al, in *Human Retroviruses* Cullen (ed), IRL Press/Oxford Univ. Press (New York, 1993) pp. 159–192

Goldberg et al, *Am. J. Dermatopathol.* 8:326–330 (1986)

Hall et al, *Science* 253:317–320 (1991)

Hall et al, *J. Virol.* 66:2456–2463 (1992)

Hall et al, *J. AIDS & Human Retrovir.* 13(Sup 1):S204–S214 (1996)

Handfield-Jones et al, *Clin. Exp. Dermatol.* 17:374–375 (1992)

Hinuma et al, *Proc. Natl. Acad. Sci. USA* 78:6476–6480 (1981)
Hirose et al, *Virology* 162:487–489 (1988)
Iwakura et al, *Int. J. Cancer* 45:980–983 (1990
Iwakura et al, *Science* 253:1026–1028 (1991)
Iwakura et al, *J. Immunol.* 155:1588–1598 (1995)
Jeang et al, *J. Virol* 61:708–713 (1987
Kamihira et al, *Jpn. J. Cancer Res.* 80:1066–1071 (1989)
Kanner et al., *J. Immunol.* 137:674–678 (1986)
Kashiwagi et al, *J. Infect. Dis.* 161:426–429 (1990
Khan et al, *J. Invest. Dermatol.* 106:667–672 (1996)
Kinoshita et al, *Gann* 75:103–105 (1984)
Kitajima et al., *Molecular and Cellular Probes,* 2:39–46 (1988)
Kitajima et al, *J. Clin. Invest.* 88:1315–1322 (1991)
Korber et al, *J. Virol.* 65:5471–5476 (1991)
Kwok et al, *J. Inf. Dis.* 158:1193–1197 (1988)
Lal, R. B, *J. AIDS & Human Retrovir.* 13(Sup. 1):S170–178 (1996)
Lambroza et al, *J. Am. Acad. Dermatol.* 32:987–993 (1995)
Lee et al, *Lancet* 337:1435–1439 (1991)
Lee et al, *Virology* 196:57–69 (1993)
Manca et al, *J. Exp. Med.* 180:1973–1978 (1994)
Mariette et al, *Arthr. & Rheum.* 36:1423-1428 (1993)
McCallum et al, *Adv. In Rheumatol.* 81:261–276 (1997)
Misch et al, *Clin. Exp. Dermatol.* 12:53–55 (1987)
Miyoshi et al, *Nature* 294:770–771 (1981)
Mochizuki et al, *Am. J. Ophthamol.* 114:123–129 (1992)
Movat, A M, *Immunology Today* 8:93–98 (1987)
Myrie et al, *Am. J. Pathol.* 99:243–252 (1980)
Nerenberg et al, *Science* 237:1324–1329 (1987)
Nishioka, K., *J. AIDS & Human Retrovir.* 13(Sup 1):S57–S62 (1996)
Ohshima et al, *Cancer Res.* 51:4639–4642 (1991)
Okayama et al, *Blood* 78:3323–3329 (1991)
Osame et al, *Lancet* I:1031–1032 (1986)
Osame et al, *Ann. Neurol.* 21:117–122 (1987)
Pancake et al, *J. Clin. Invest.* 95:545–554 (1995)
Pancake et al, *J. AIDS & Human Retrovir.* 13:314–319 (1996a)
Pancake et al, *Blood* 88:3004–3009 (1996b)
Poiesz et al, *Proc. Natl. Acad. Sci. USA* 77:7415–7419 (1980)
Popovic et al, *Science* 219:856–859 (1983)
Ramirez et al, *J. Clin. Mircorbiol.* 36:1811–1813 (1998)
Ratnam et al, *J. Eur. Acad. Dermatol. Venereol.* 3:505–510 (1994)
Sawada et al, *Jpn. J. Cancer Res.* 80:506–508 (1989)
Saxinger et al, *Laboratory Investigation* 49:371–377 (1983)
Saxon et al, *Ann. Int. Med.* 88:323–326 (1978)
Seiki et al, *Proc. Natl. Acad. Sci. USA* 80:3618–3622 (1983)
Shimotohno et al, *Proc. Natl. Acad. Sci. USA* 82:3101–3105 (1985)
Shioiri et al, *Int. J. Cancer* 53:1–4 (1993)
Sigal et al, *Clin. Exp. Dermatol.* 12:453–454 (1987)
Smith et al, *Gene* 67:31–40 (1988)
Sodroski et al, *Science* 225:381–385 (1984)
Sumida et al, *Arthr. & Rheum.* 37:545–550 (1994)
Terada et al, *Lancet* 344:1116–1119 (1994)
Vanderlugt et al, *Current Opinion in Immunol.* 8:831–839 (1996)
Von Herrath et al, *Current Opinion in Immunol.* 8:878–885 (1996)
Wattel et al, *J. AIDS & Human Retrovir.* 13(supl):S92–S99 (1996)
Weiner et al, *Ann. Rev. Immunol.* 12:809–837 (1994)
Williams et al, *Science* 240:643–646 (1988)
Wong-Staal et al, *Nature* 302:626–628 (1983)
Yoshida, M., in *The Molecular Basis of Blood Diseases*, Stamatoyannopoulos et al (eds), W. B. Saunders (Philadelphia) pp. 929–941
Yoshida et al, *Curr. Topics in Microbiol. & Immunol.* 115:157–175 (1985)
Zackheim et al, *J. Am. Acad. Dermatol.* 6:340–345 (1982)
Zackheim et al, *J. Am. Acad. Dermatol.* 36:557–562 (1997)
Zucker-Franklin et al, *Proc. Natl. Acad. Sci. USA* 71:1877–1881 (1974)
Zucker-Franklin et al, *Proc. Natl. Acad. Sci. USA* 88:7630–7634 (1991)
Zucker-Franklin et al, *Blood* 80:1537–1545 (1992)
Zucker-Franklin et al, *AIDS Res. Human Retroviruses* 10:1173–1177 (1995)
Zucker-Franklin et al, *Proc. Natl. Acad. Sci. USA* 94:6403–6407 (1997a)
Zucker-Franklin et al, *Lancet* 349:999 (1997b)
Zucker-Franklin et al, *Clin. Diagnostic Lab. Immunology* 5:831–835 (1998)

What is claimed is:

1. A method for screening healthy blood donors or potenial blood donors for carriers of diseases or conditions related to at least one of HTLV-I and HTLV-II infections comprising:

testing a sample from a donor or a potential donor for the presence of a DNA SEQ ID NO: 1 or SEQ ID NO: 2 respectively which encodes the HTLV-I tax protein or the HTLV-II tax protein;

wherein a positive test for the presence of a DNA which encodes the HTLV-I tax protein or the HTLV-II tax protein indicates the presence of:

a. at least one of HTLV-I tax protein or HTLV-II tax protein;

b. DNA which encodes at least one of HTLV-I tax protein or HTLV-II tax protein; and c. antibodies specific to at least one of HTLV-I tax protein or HTLV-II tax protein; and if the test for at least one of (a), (b), or (c) is positive, concluding that the donor or potential donor is a carrier of a disease or condition relate to at least one of HTLV-I or HTLV-II infection;

wherein the donor or potential donor had not been tested for antibodies to at least one of HTLV-I or HTLV-II.

* * * * *

SEQUENCE LISTING

```
<160> NUMBER OF SEQ ID NOS: 11

<210> SEQ ID NO 1
<211> LENGTH: 54
<212> TYPE: DNA
<213> ORGANISM: Homo sapiens

<400> SEQUENCE: 1

aaggcgactg gtgccccatc tctgggggac tatgttcggc ccgcgcttga ttca          54


<210> SEQ ID NO 2
<211> LENGTH: 50
<212> TYPE: DNA
<213> ORGANISM: Homo sapiens

<400> SEQUENCE: 2

ctacatcgtc acgccctact ggccacctgt ccagagcatc agatatccac              50
```

-continued

<210> SEQ ID NO 3
<211> LENGTH: 66
<212> TYPE: DNA
<213> ORGANISM: Homo sapiens

<400> SEQUENCE: 3
aaggcgactg gtgccccatc tctgggggac tatgttcggc ccgcgcttat tcatttgctt 60
gattca 66

<210> SEQ ID NO 4
<211> LENGTH: 60
<212> TYPE: DNA
<213> ORGANISM: Homo sapiens

<400> SEQUENCE: 4
ctacatcgtc acgccctact ggccacctgt ccagagcatc agatatccac atcaatccac 60

<210> SEQ ID NO 5
<211> LENGTH: 20
<212> TYPE: DNA
<213> ORGANISM: Homo sapiens

<400> SEQUENCE: 5
cccatcttac gttccctagc 20

<210> SEQ ID NO 6
<211> LENGTH: 20
<212> TYPE: DNA
<213> ORGANISM: Homo sapiens

<400> SEQUENCE: 6
ggatcttgac atagggggca 20

<210> SEQ ID NO 7
<211> LENGTH: 26
<212> TYPE: DNA
<213> ORGANISM: Homo sapiens

<400> SEQUENCE: 7
acatggagtc gggactgcac ccagcc 26

<210> SEQ ID NO 8
<211> LENGTH: 17
<212> TYPE: DNA
<213> ORGANISM: Homo sapiens

<400> SEQUENCE: 8
tcacgggttt cccaact 17

<210> SEQ ID NO 9
<211> LENGTH: 26
<212> TYPE: DNA
<213> ORGANISM: Homo sapiens

<400> SEQUENCE: 9
tgtcaaaaat caagtctccc ctagcc 26

<210> SEQ ID NO 10
<211> LENGTH: 20
<212> TYPE: DNA
<213> ORGANISM: Homo sapiens -continued

```
<400> SEQUENCE: 10

cgtgtttgga gactgtgtac                                                  20


<210> SEQ ID NO 11
<211> LENGTH: 20
<212> TYPE: DNA
<213> ORGANISM: Homo sapiens

<400> SEQUENCE: 11

catcgatggg gtcccaggtg                                                  20
```